(12) United States Patent
Robertson et al.

(10) Patent No.: US 11,678,835 B2
(45) Date of Patent: Jun. 20, 2023

(54) MINIMAL MATERIAL EAR SENSOR SYSTEM

(71) Applicant: NextSense, Inc., Mountain View, CA (US)

(72) Inventors: Nick Robertson, Santa Clara, CA (US); Russell Mirov, Los Altos, CA (US); John Stivoric, Pittsburgh, PA (US)

(73) Assignee: NextSense, Inc., Mountain View, CA (US)

( * ) Notice: Subject to any disclaimer, the term of this patent is extended or adjusted under 35 U.S.C. 154(b) by 282 days.

(21) Appl. No.: 16/868,573

(22) Filed: May 7, 2020

(65) Prior Publication Data

US 2021/0145351 A1 May 20, 2021

Related U.S. Application Data

(60) Provisional application No. 62/936,884, filed on Nov. 18, 2019.

(51) Int. Cl.
*A61B 5/00* (2006.01)
*A61N 1/05* (2006.01)
(Continued)

(52) U.S. Cl.
CPC .............. *A61B 5/411* (2013.01); *A61B 5/291* (2021.01); *A61F 2/18* (2013.01); *A61F 11/20* (2022.01); *A61N 1/0541* (2013.01)

(58) Field of Classification Search
CPC ... A61B 5/0205; A61B 5/02438; A61B 5/291; A61B 5/316; A61B 5/411; A61B 5/4812;
(Continued)

(56) References Cited

U.S. PATENT DOCUMENTS 7,654,997 B2 2/2010 Makower et al.
9,782,584 B2 10/2017 Cartledge et al.
(Continued)

FOREIGN PATENT DOCUMENTS

WO 2018103861 A1 6/2018

OTHER PUBLICATIONS

International Search Report and Written Opinion for Application No. PCT/US2020/032327 dated Jul. 23, 2020.
(Continued)

*Primary Examiner* — Christopher A Flory
(74) *Attorney, Agent, or Firm* — Perkins Coie LLP

(57) ABSTRACT

The technology involves scaffold structures used for in-ear sensor systems. Such systems that can perform biometric signal detection or act as a human-computer interface. Scaffolding arrangements minimize the amount of material placed in the ear while providing a secure fitting device that can be worn for hours, days or longer in order to provide maximal benefit to the wearer. The scaffolding includes a "C"-shaped arcuate curvature for at least part of the housing. This configuration can act as a natural leaf spring to help maintain the housing in contact with different points along the ear. Sensors are located along various points of the scaffolding for use in different diagnostic situations. Different components of an on-board sensor input and processing system can be distributed along different parts of the scaffolding. Such structures beneficially minimize ambient sound occlusion and avoid the need of an exterior strap or clip worn around the ear.

20 Claims, 10 Drawing Sheets

(51) Int. Cl.
  *A61F 2/18* (2006.01)
  *A61B 5/291* (2021.01)
  *A61F 11/20* (2022.01)

(58) Field of Classification Search
  CPC ..... A61B 5/681; A61B 5/6815; A61B 5/6816; A61B 5/6817; A61B 5/6831; A61F 11/20; A61F 2/18; A61N 1/0541
  See application file for complete search history.

(56) References Cited

U.S. PATENT DOCUMENTS

| | | | | |
|---|---|---|---|---|
| 2009/0129615 | A1 | 5/2009 | Kasanmascheff | |
| 2012/0095527 | A1 | 4/2012 | Vardi et al. | |
| 2012/0209101 | A1 | 8/2012 | Kidmose et al. | |
| 2016/0166203 | A1* | 6/2016 | Goldstein | H04R 25/00 600/509 |
| 2017/0087364 | A1* | 3/2017 | Cartledge | A61N 1/18 |
| 2019/0116415 | A1* | 4/2019 | Qian | H04R 1/105 |
| 2019/0223747 | A1* | 7/2019 | Chou | A61B 5/6816 |
| 2019/0380597 | A1* | 12/2019 | Howard | A61B 5/318 |
| 2020/0133021 | A1* | 4/2020 | Belli | G02C 5/143 |

OTHER PUBLICATIONS

Kappel, Simon L, et al., "Real-Life Dry-Contact Ear-EEG", 2018 40th Annual International Conference of the IEEE Engineering in Medicine and Biology Society (EMBC), IEEE, Jul. 18, 2020., pp. 5470-5474.
Mikkelsen, Kaare B., et al., "Accurate whole-night sleep monitoring with dry-contact ear-EEG", Scientific Reports, vol. 9, No. 1, Nov. 14, 2019.
X3 Jaybird User Guide, retrieved from the internet 2019, pp. 1-26.
Dong, Hao, et al., A New Soft Material Based In-the-Ear EEG Recording Technique, 2016 IEEE, pp. 5709-5712.
Jung, Ha-Chul, et al., CNT/PDMS Composite Flexible Dry Electrodes for Long-Term ECG Monitoring, IEEE Transactions on Biomedical Engineering, vol. 59, No. 5, May 2012, pp. 1472-1479.
Kidmose, P., et al., Ear-EEG from generic earpieces: A feasibility study, 35th Annual International Conference of the IEEE EMBS, Osaka, JP 2013, pp. 543-546.
Lee, Joong Hoon, et al., CNT/PDMS-based canal-typed ear electrodes for inconspicuous EEG recording, Journal of Neural Engineering, 11, (2014), pp. 1-11.
Looney, D., et al., An In-The-Ear Platform For Recording Electroencephalogram, 33rd Annual International Conference of the IEEE EMBS, Boston, MA, 2011, pp. 6882-6885.
Looney, David, et al., The In-the-Ear Recording Concept, IEEE Pulse, 2012, pp. 32-42.
Mannoor, Manu S., et al., 3D Printed Bionic Ears, NIH Public Access, Nano Lett. 2013, 13(6), pp. 1-12.

* cited by examiner

150

100

210

200

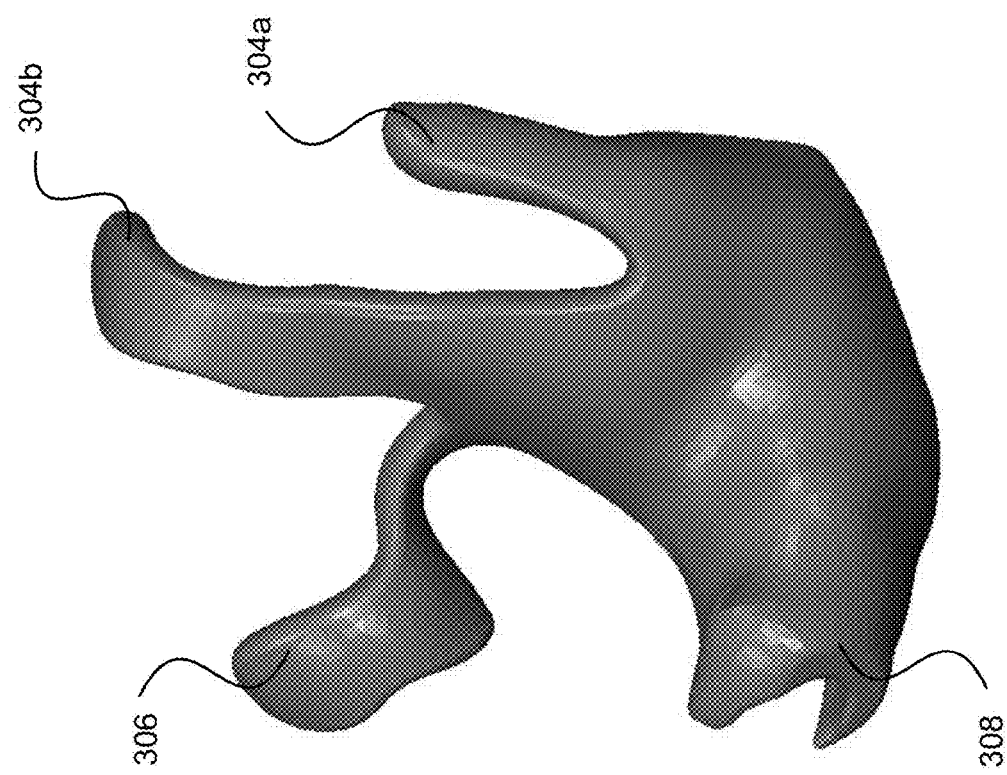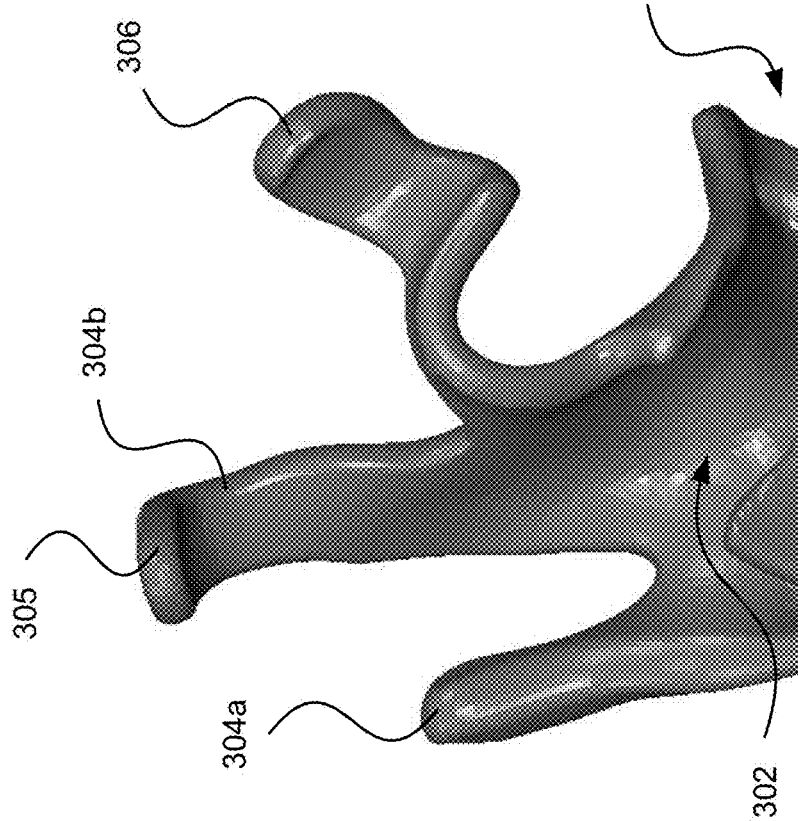

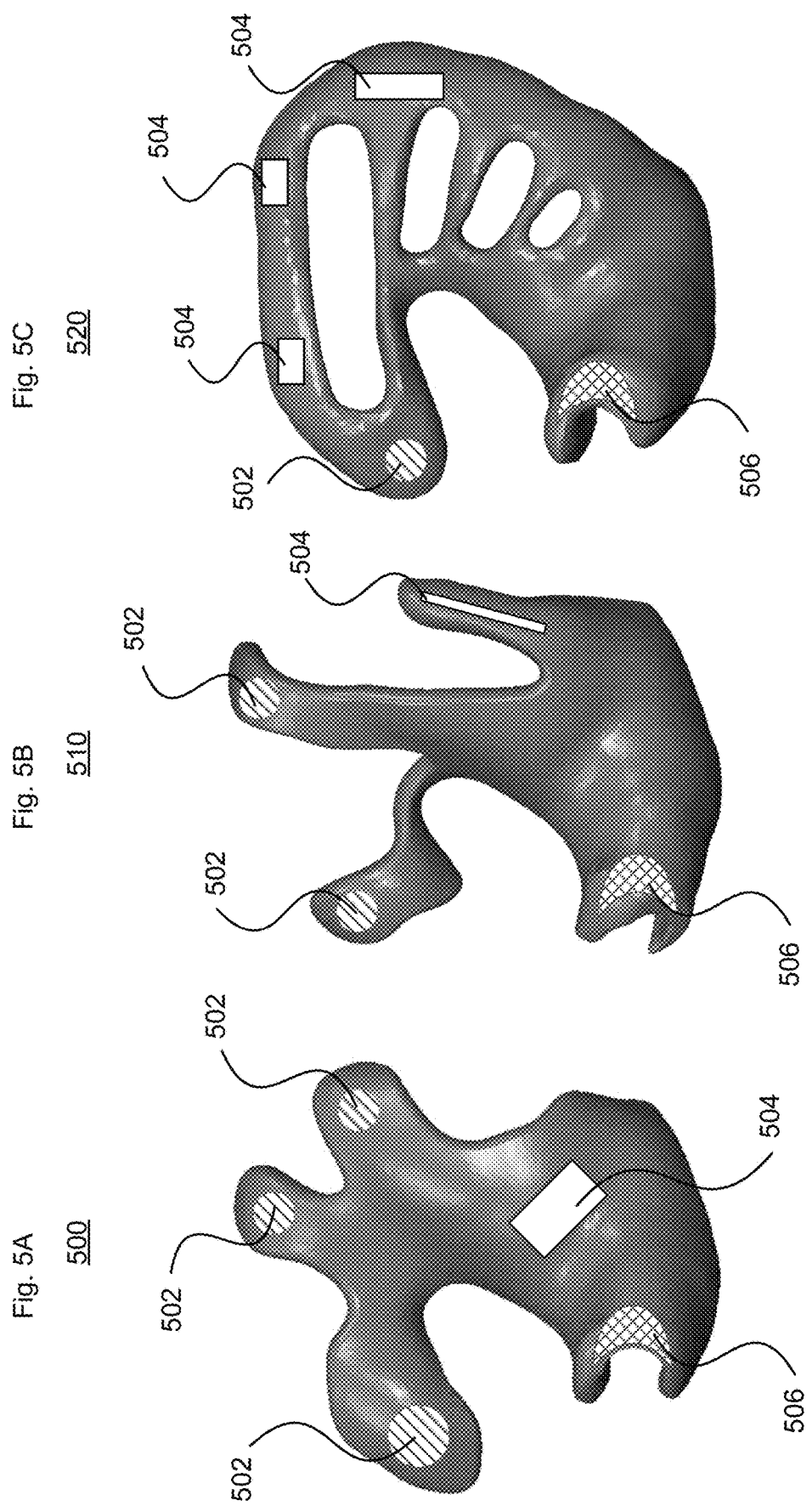

MINIMAL MATERIAL EAR SENSOR SYSTEM

CROSS-REFERENCE TO RELATED APPLICATIONS

This application claims the benefit of the filing date of U.S. provisional application No. 62/936,884, filed Nov. 18, 2019, the entire disclosure of which is incorporated herein by reference.

BACKGROUND

Wearable sensors have been used to detect electroencephalogram (EEG) and other bio signals from the wearer's body. These signals can be used for medical or non-medical (e.g., brain control interface) purposes. In the past, caps have been worn on the head to capture EEG signals. These caps can capture input via multiple data channels. However, wearing a cap for an extended period of time can be cumbersome and uncomfortable. It can also be difficult to get high quality signals, especially if the wearer has thick hair. In-ear sensors, for instance using custom-molded earpieces, have also been considered. These devices may have a rigid hearing aid type arrangement fabricated using a cast shape or a digital scan of the wearer's ear canal, which can be costly and time consuming. More recently, malleable sensors with one or more electrical contacts have been proposed, which attempt to locate electrodes at particular points in the ear and are tied to specific medical applications. Such approaches suffer from various drawbacks, including difficulty providing multiple high quality in-ear contacts, partially or completely blocking ambient sounds, and costly and labor-intensive manufacturing techniques.

BRIEF SUMMARY

The technology relates to in-ear sensors that can be used for biometrics such as an EEG or magnetoencephalograph (MEG) signal detection, or a human-computer interface. Scaffold structures are provided that minimize the amount of material required, while providing a secure fitting device that can be worn for hours, days or longer in order to provide maximal benefit to the wearer. Such structures are able to minimize the occlusion of ambient sound, so the wearer can easily hear what is going on around him or her. The scaffold structures disclosed herein provide sensor assemblies with multiple points of contact within the ear so that the assemblies stay in place. Various material configurations can be employed so that the assemblies are as comfortable and unobtrusive as possible.

As noted above, a custom in-ear device can be made according to a detailed scan of the ear. However, this approach may not a feasible solution for high volume manufacturing. Furthermore, the ear is flexible and different surfaces can change shape and/or orientation depending on what the wearer is doing (e.g., rolling over while sleeping). Thus, even a custom fit device may not be able to avoid sound occlusion or maintain the desired points of contact. And while certain wireless headphones or earpieces include an over the ear loop or strap to keep the acoustical components secured to the ear, these types of configurations are not conducive to long-term or unobtrusive wear. In contrast, the scaffolding-based sensor assemblies provided herein can be mass produced in a cost-effective manner, while providing wearer comfort and enabling biometric and/or computer interface solutions.

According to one aspect of the technology, a sensor assembly is configured for partial or complete insertion in an ear of a wearer. The sensor assembly comprises a central C-shaped body, one or more sensors, and circuitry. The central C-shaped body comprises one or more materials, and provides a spring force so that the sensor assembly maintains multiple points of contact along the ear of the wearer. The one or more sensors are disposed along the sensor assembly and attached to the central C-shaped body. The one or more sensors are configured to detect bio-signals via the ear of the wearer. The circuitry is attached to the central C-shaped body and is operatively coupled to the one or more sensors. The circuitry includes a processing device configured to receive the detected bio-signals from the one or more sensors and to perform on-board processing of the received bio-signals or to transmit the received bio-signals to a remote processing system. Furthermore, the central C-shaped body is configured to avoid sound occlusion by the sensor assembly when worn in the ear of the wearer.

In one example, the central C-shaped body is configured to self-center the sensor assembly in the ear of the wearer. In another example, the sensor assembly further comprises a plurality of protrusions extending from the central C-shaped body. Here, the one or more sensors may be disposed along the protrusions.

In another example, the sensor assembly further comprises an extension extending from the central C-shaped body. The extension is configured to extend at least partly into the ear canal during wear. One or more protrusions may project away from the central C-shaped body at an angle relative to the extension. The one or more sensors may be disposed along at least one of the extension and the one or more protrusions. A first one of the one or more protrusions may form a first end of the C-shaped body. In this case, the extension forms an opposing, second end of the C-shaped body.

According to another example, the central C-shaped body may include a series of openings along the body disposed therealong. The one or more materials may include a first material having a first hardness and a second material having a second hardness less than the first hardness. For instance, the first material may form a base layer of the C-shaped body, and the second material may be over-molded on the first material. In any of these configurations, the C-shaped body can be formed by 3D printing or injection molding.

The one or more materials may include one or more bio-compatible materials arranged along points of contact with the ear of the wearer. The circuitry may include a plurality of components distributed along different areas of the central C-shaped body. The C-shaped body may be configured to provide the spring force at different anchor points about one or more of the ear's helix, antihelix, concha or opening to the ear canal.

In another example, an extension of the C-shaped body has a channel that extends at least partly into the ear canal. For instance, the channel may extend along the first bend of the ear canal. In some arrangements, the channel may extend past the first bend and at least partly along the second bend of the ear canal.

In yet another example, the C-shaped body is at least partly covered by a chromogenic material configured to change color in response to a stimulus.

According to other aspects of the technology, a sensor system is configured to detect and process bio signals of a wearer. Here, the sensor system comprises the sensor assembly in any of the arrangements described herein, along with a remote processing system. The remote processing system includes a transceiver configured for communication with a transceiver of the sensor assembly, and one or more processors configured to process the bio signals received from the sensor assembly.

BRIEF DESCRIPTION OF THE DRAWINGS

FIGS. 3A-E illustrate another example scaffolding structure in accordance with aspects of the technology.
FIGS. 5A-C illustrate example sensor placement for different scaffolding structures in accordance with aspects of the technology.

DETAILED DESCRIPTION

Figure 1B:
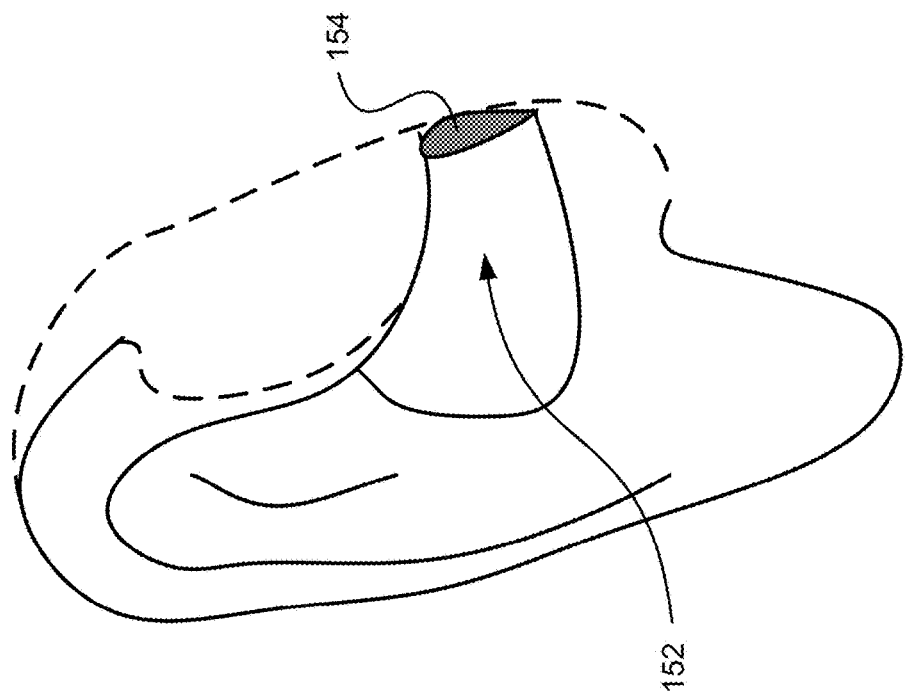
FIGS. 1A-B illustrate an example human ear.
Figure 1A:
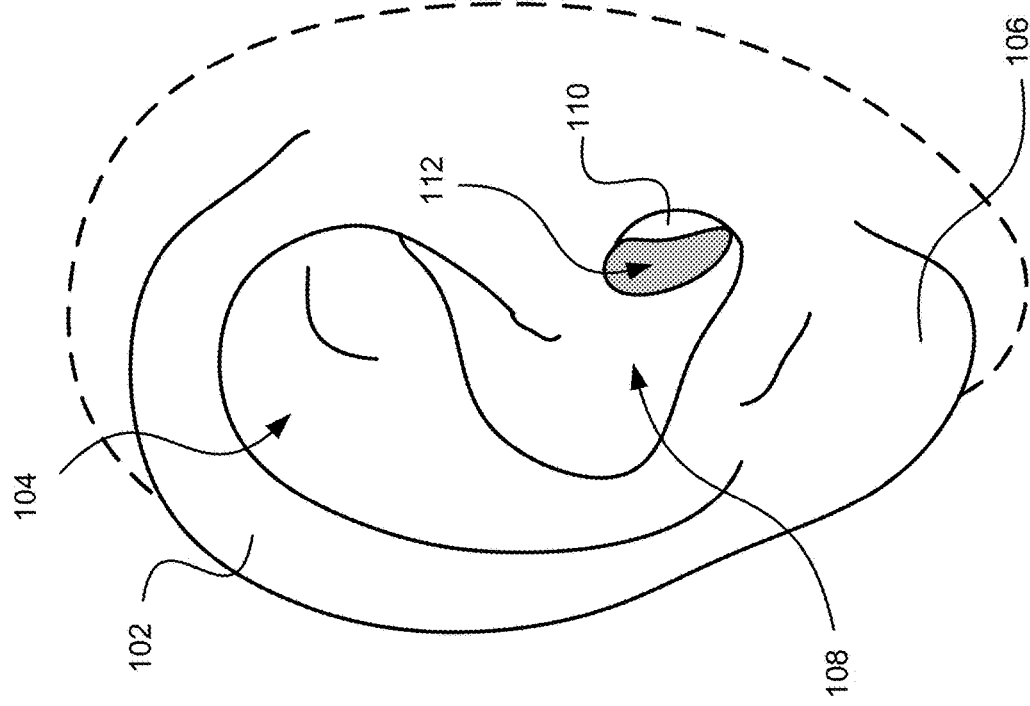

The human ear is a complex organ that includes three main parts, the outer ear, middle ear and inner ear. An example of the outer ear (auricle or pinna) is illustrated in view 100 of FIG. 1A. As shown, the outer ear includes a helix 102, antihelix 104, lobule 106, concha 108, tragus 110 and opening to the ear canal 112. FIG. 1B illustrates another view 150 showing a partial cutaway perspective to illustrate the outer portion of the ear canal 152 leading to the ear drum (tympanic membrane) 154. It can be seen that the outer ear and ear canal are complex, three-dimensional structures. Furthermore, the outer ear is formed of cartilage and skin, which means that it is a flexible organ. Thus, if the person is wearing a hat or helmet, or rolls over in his or her sleep, the shape of the outer ear can change. As a result, an effective in-ear sensor assembly needs to conform to the changeable 3D shape while providing sufficient points of contact for the on-board sensors.

The approaches in this case provide scaffolding-type "skeleton" structures for in-ear sensor assemblies that minimize sound occlusion. The general architectures are illustrated in the accompanying figures, and are discussed further below. The objective is to keep the electrodes for the on-board sensor(s) in contact with the skin of the ear, and provide as many contact points in the correct areas as the electronics dictate for the signals of interest.

These scaffolding arrangements have a "C"-shaped arcuate curvature for at least part of the housing. This can act as a natural leaf spring to provide a spring force, which helps maintain the housing in contact with different points along the outer ear. In particular, the scaffolding is able to push against the skin, for instance at different locations (anchor points) about the helix, antihelix, concha (e.g., concha bowl), and/or opening to the ear canal, while also being able to move while the ear moves. Pushing against the ear can actually make things more comfortable for the wearer, and also provide better sensor connections for measurement purposes. Also, this general shape can help self-center the device when placed in the ear.

Sensors can be located along various points of the scaffolding for use in EEG, MEG or other diagnostic situations. For instance, Alpha waves on the order of 8-12 Hz can be detected either by either EEG or MEG. In addition, lower frequency signals (e.g., Delta waves between 0.5-3 Hz or Theta waves between 3-8 Hz) and/or higher frequency signals (e.g., Beta waves between 12-38 Hz or Gamma waves between 38-42 Hz) may also be detected. One or more of these types of signals can be evaluated and analyzed either alone or in conjunction with other data to provide information (e.g., biomarkers) about the wearer. The other data may be obtained by additional in-ear sensors (e.g., in the same assembly or in a sensor assembly worn in the other ear) or sensors located elsewhere on or near the wearer. These may include heart rate and temperature sensors. Electrodermal activity (EDA) sensors that detects skin potential, resistance, conductance, admittance, or impedance, such as galvanic skin response sensors, may also be employed. Furthermore a pulse oximeter sensor, a glucometer, orientation sensors, location sensors and/or accelerometers can also be used. These sensors can be used in any combination. The biomarkers or other information can be evaluated to help classify mental or emotional states, as well as activities of daily living.

For sensors to pick up signals of interest with high fidelity while rejecting or minimizing noise, according to one aspect of the technology the scaffolding arrangements include a minimum of two electrodes. For example, a first electrode may be placed as close to the brain as possible, for instance along the ear canal wall. A second electrode can be placed such that it detects the same types of signals as the first, e.g., along the concha, but potentially with some attenuation of the desired signal. This approach allows a differential amplifier to reject common mode interference. A third electrode can be place relatively far from the first and/or second electrodes, for instance along the antihelix or potentially at a different location on the other ear. Here, the third electrode may be used as a "right leg drive" (RLD) to hold the other two electrodes at a known potential relative to the sensing electronics.

Example Structures

Various configurations of an in-ear sensor assembly will now be described in accordance with aspects of the technology.

Figure 2B:
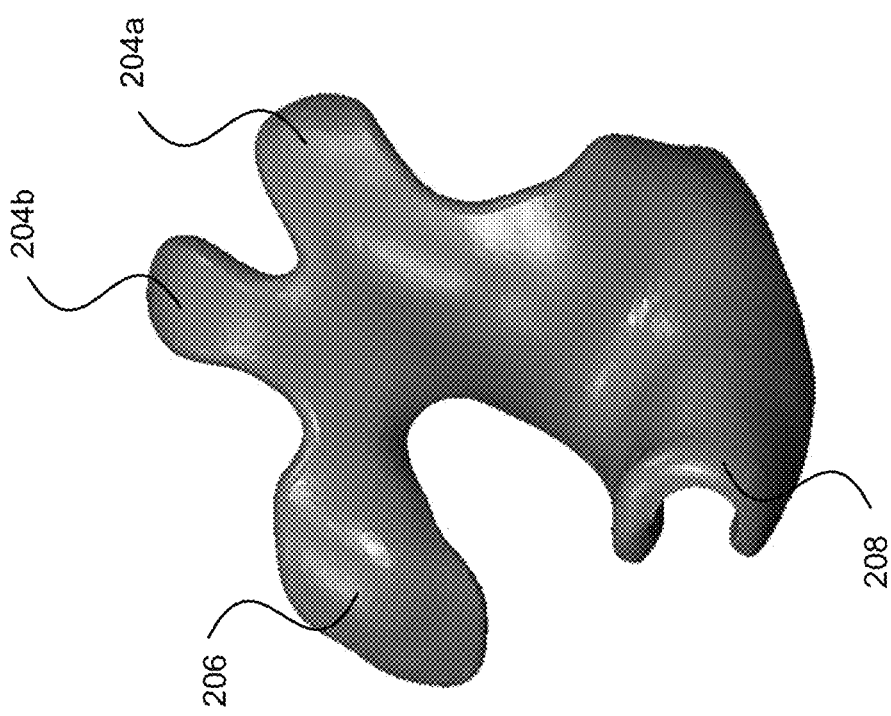
FIGS. 2A-E illustrate one example scaffolding structure in accordance with aspects of the technology.
Figure 2A:
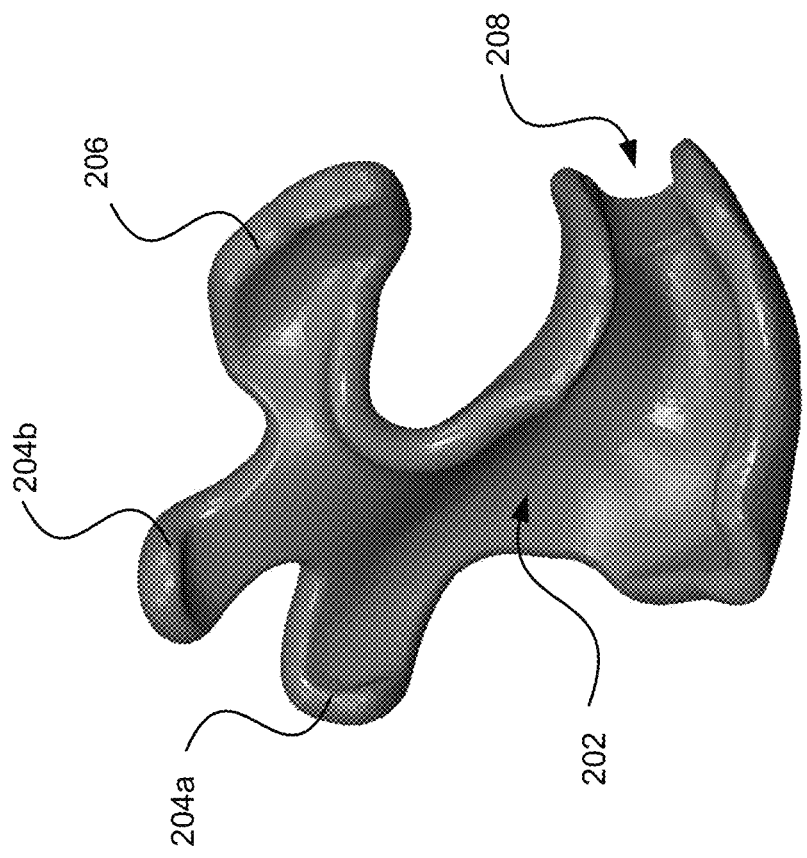
Figure 2E:
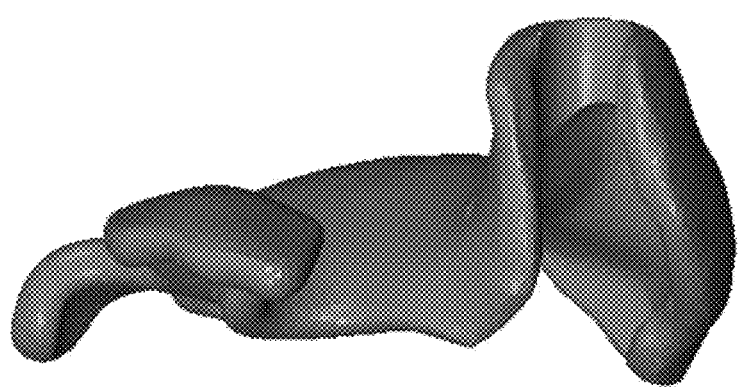
Figure 2D:
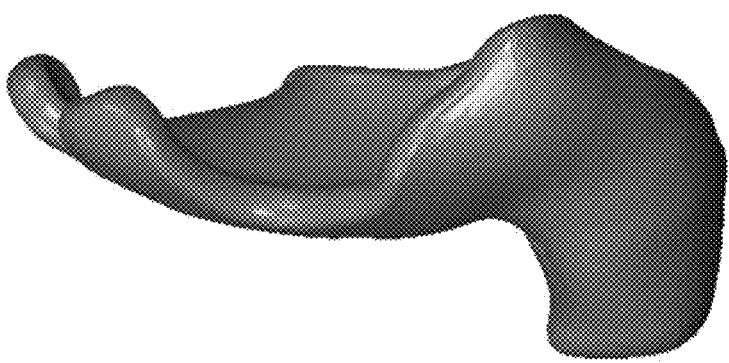
Figure 2C:
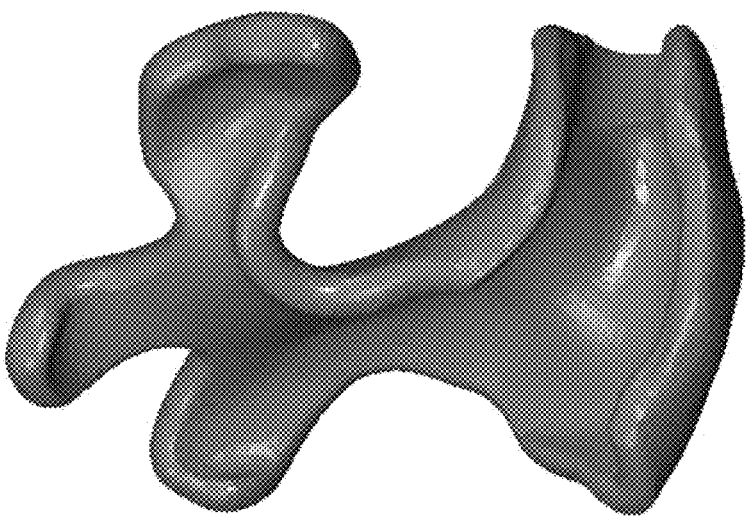

The example scaffolding structure of FIGS. 2A-E has a central C-shaped body with a plurality of fingers or other projections extending outward from the larger side of the C. In particular, FIG. 2A is a front view 200 of the side of the scaffolding structure that generally faces away from the outer ear, while FIG. 2B is a rear view 210 of the scaffolding structure with surfaces that generally contact different parts of the outer ear and ear canal. FIG. 2C is a front perspective view 220, FIG. 2D is a left side view 230, and FIG. 2E is a right side view 240.

As shown in FIG. 2A, central body 202 is a solid, unitary element without any openings. Protrusions 204a and 204b may contact selected points along the outer ear adjacent to the helix region. The protrusions 204 may extend radially from the central body 202. Protrusion(s) 206 may also contact a section of the outer ear adjacent to the helix region, such as along the navicular fossa. In this example, the protrusion 206 may be perpendicular or at another angle relative to the protrusions 204, and form the upper part of the "C". Extension 208 forms the opposite end of the "C". As shown in FIGS. 2A-E, the extension 208 is also curved with a "C" or open semi-cylindrical shape configured to extend at least partly into the ear canal, for instance along first bend, or alternatively extending at least 10-30% along the second bend.

Figure 3E:
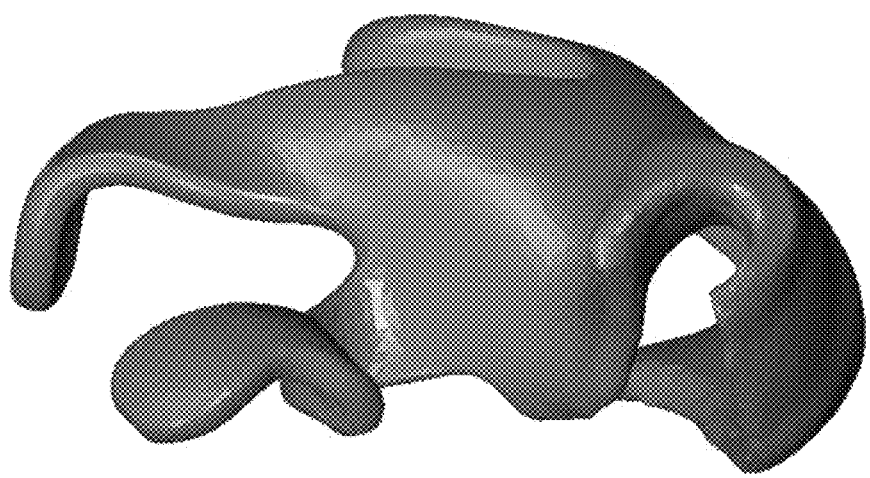
Figure 3D:
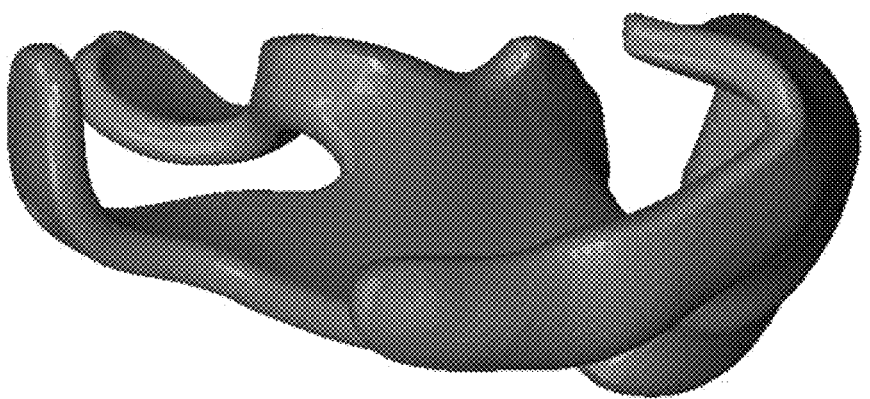
Figure 3C:
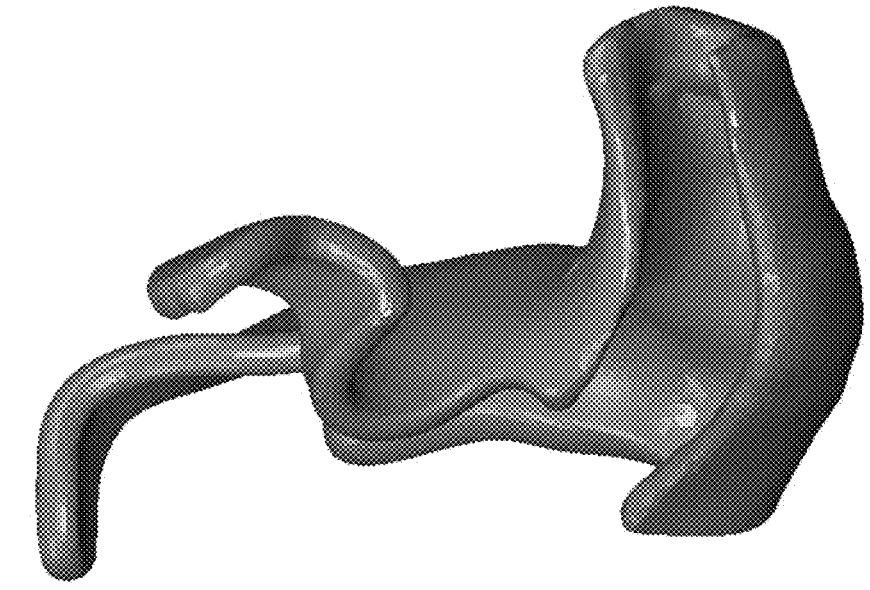

The example scaffolding structure of FIGS. 3A-E is similar to the structure of FIGS. 2A-E, in that it has a central C-shaped body with a plurality of fingers or other projections extending outward from the larger side of the C. In particular, FIG. 3A is a front view 300 of the side of the scaffolding structure that generally faces away from the outer ear, while FIG. 3B is a rear view 310 of the scaffolding structure with surfaces that generally contact different parts of the outer ear and ear canal. FIG. 3C is a front perspective view 320, FIG. 3D is a left side view 330, and FIG. 3E is a right side view 340.

As shown in FIG. 3A, central body 302 is a solid, unitary element without any openings, although it may be formed with less surface area than central body 202. Protrusions 304a and 304b may contact selected points along the outer ear adjacent to the helix region. The protrusions 304 may extend from the central body 302, for instance parallel to one another. As shown, the upper end 305 of protrusion 304b may be at an angle, for example to contour along the helix region. Protrusion(s) 306 may also contact a section of the outer ear adjacent to the helix region, such as along the navicular fossa. In this example, the lower section of protrusion 306 may be perpendicular or at another angle relative to the protrusions 304 and form the upper part of the "C", while the upper section of protrusion 306 may extend radially from the lower section. In this case, the protrusions 304 and 306 extend farther from the central body 302 than the protrusions 204 and 206 do from the central body 202. Similar to extension 208, extension 308 forms the lower, opposite end of the "C". As shown in FIGS. 3A-E, the extension 308 is also curved with a "C" or open semi-cylindrical shape configured to form a semicircular channel that extends at least partly into the ear canal, for instance along first bend, or alternatively extending at least 10-30% along the second bend.

The two arrangements in FIGS. 2A-E and 3A-E have the benefit of providing complementary/opposing spring features disposed along different parts of the ear. This can help maintain the device in place as the wearer moves and the ear changes shape. By way of example, three opposing equal points of contact will keep an object at rest in each plane. In a 3D structure like in the outer ear, more points of contact in different planes assist in maintaining the device in position. As long as the forces oppose each other and cancel each other out, the sensor assembly should stay at rest and steady.

Figures 4A, 4B:
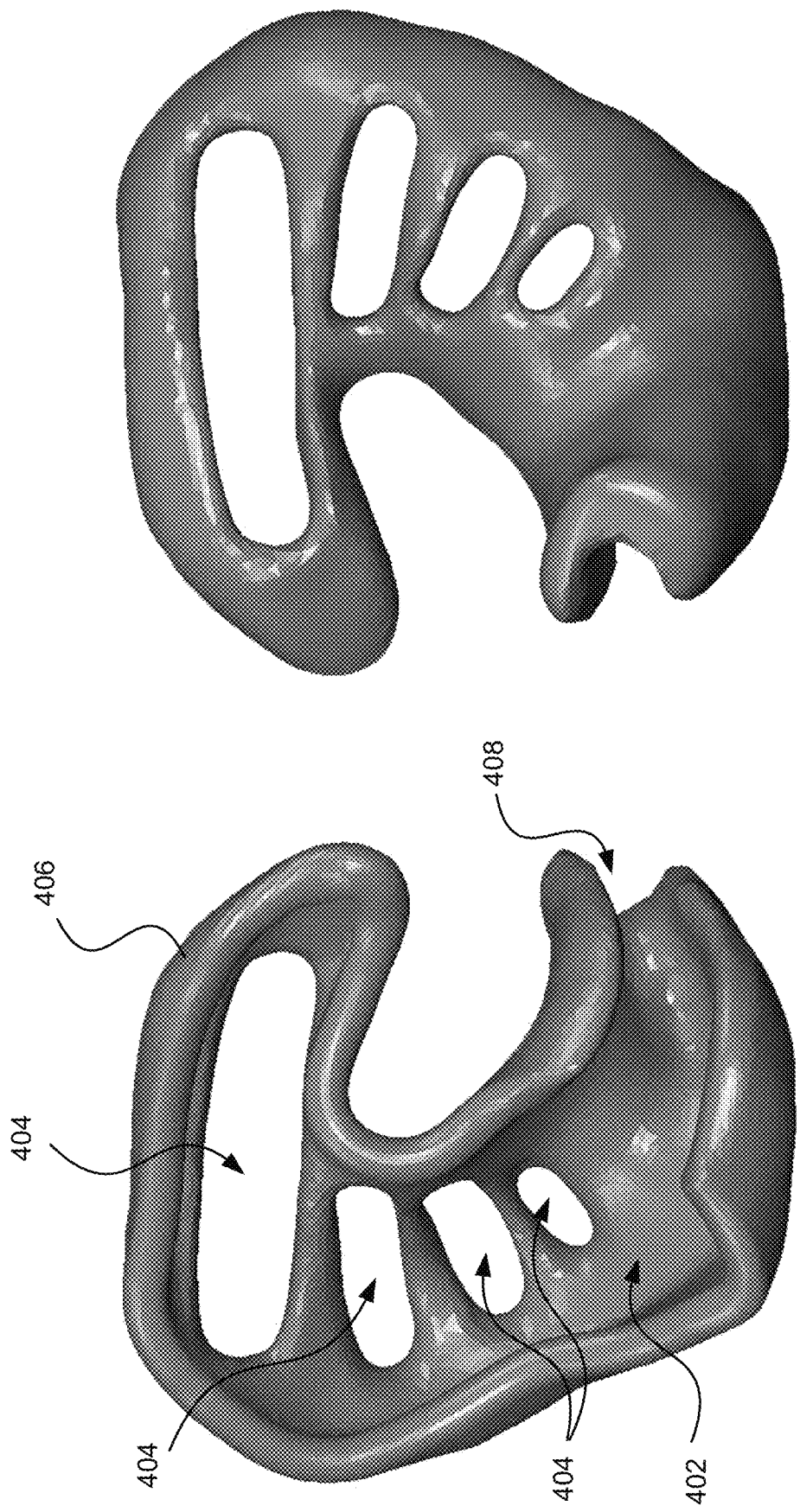
FIGS. 4A-E illustrate a further example scaffolding structure in accordance with aspects of the technology.
Figure 4E:
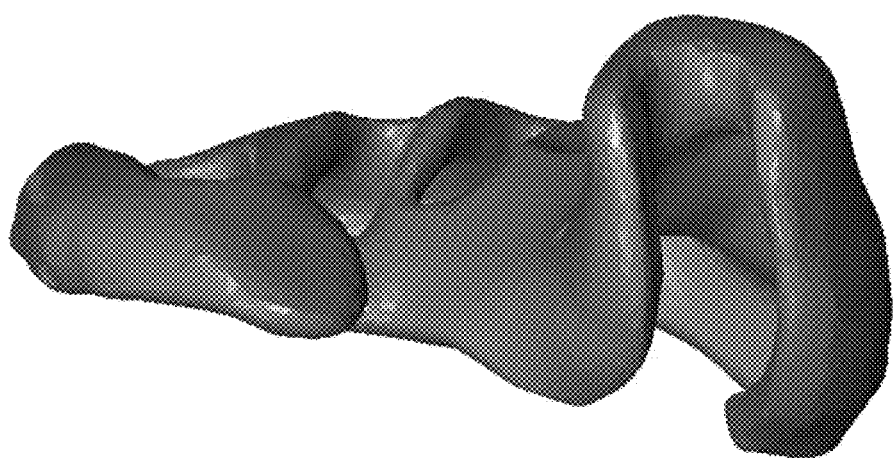
Figure 4D:
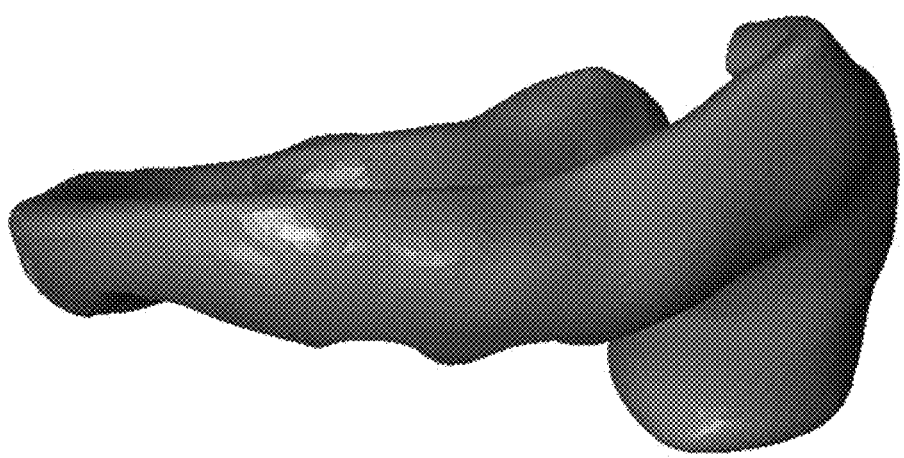
Figure 4C:

The example scaffolding structure of FIGS. 4A-E also has a central C-shaped body. In particular, FIG. 4A is a front view 400 of the side of the scaffolding structure that generally faces away from the outer ear, while FIG. 4B is a rear view 410 of the scaffolding structure with surfaces that generally contact different parts of the outer ear and ear canal. FIG. 4C is a front perspective view 420, FIG. 4D is a left side view 430, and FIG. 4E is a right side view 440.

In this structure, unlike the examples of FIGS. 2A-E and 3A-E, there are no projections extending from central body 402. Also, the central body 202 does not has a solid, continuous surface of material. As best seen in FIGS. 4A-B, there are a series of openings 404 along the body 402 itself. Here, the openings 404 may be rounded rectangular shapes as illustrated, although other configurations are possible, for instance with different geometric shapes. Also, while the openings appear generally parallel to one another, their relative orientations and sizes may differ. While four openings 404 are provided in this example, there may be fewer (e.g., 1-3 openings) or more (e.g., 5-6, or more openings).

Section 406 is configured to contact an upper section of the outer ear adjacent to the helix region, including along the navicular fossa. In this example, the section 406 forms the upper part of the "C". And extension 408 forms the opposite end of the "C". As shown in FIGS. 4A-E, the extension 408 is also curved with a "C" or open semi-cylindrical shape configured to extend at least partly into the ear canal, for instance along first bend, or alternatively extending at least 10-30% along the second bend.

It may be desirable to allow the wearer to hear ambient sounds while the sensor assembly is worn. This will avoid the sensation of the device being an ear plug, and will be more conducive to wearing for an extended period of time (e.g., hours, days or longer). In the above examples, the extensions and other portions of the scaffolding minimize blockage of the ear canal. In one example, the extension may be made as thin as possible. In another example, the extension comprises a non-collapsible (rigid or semi-rigid) material that enables the wearer to hear ambient sounds without appreciable distortion (e.g., without cutting off or attenuating higher frequencies beyond 10-15 kHz) or reduction in volume. By way of example, the extension and/or other portions of the scaffolding may be on the order of 1.5-2.0 mm thick. In other examples, the thickness may be no more than 5.0 mm.

Fabrication

Scaffolding structures such as described above can be fabricated using different combinations and/or layers of soft, semi-soft, and hard materials of varying durometers to achieve all the needs for fit and sensing. For instance, silicone, nylon, conductive polymers and other materials can be used at different locations along the scaffolding. In one scenario, harder acrylic-like materials could be coated with softer bio-compatible materials to enhance comfort for long-term wear. In one particular example, silicone is the primary bio-compatible material that may be over-molded on an acrylic base structure. Sensor contacts may be formed in or on the silicone, with wiring printed or otherwise run along the acrylic base. There are many electrically conductive metal materials that may be arranged to have contact with the skin for the sensors. A non-exhaustive list of such metals includes silver (Ag), silver chloride (AgCl), AgAgCl, gold (Au), platinum (Pt), titanium nitride (TiN), etc. Furthermore, colors for part or all of the sensor assembly may be selected so that the device is unobtrusive and blends in with the wearer's ear.

Different manufacturing approaches may be feasible for the scaffolding. For instance, a multi-piece device can be fabricated as separate components and then snapped together or otherwise assembled. This might allow for a circuit board (or boards) to be inserted during assembly. Alternatively, 3D printing or injection molding may be employed. These techniques may provide greater flexibility when incorporating different materials. Here, the circuitry may be added as part of the manufacturing process as opposed to requiring additional assembly steps. Regardless of the manufacturing technique(s), minimizing the scaffolding material and minimizing sound occlusion are important to enable rapid fabrication and provide a compliant structure that will remain in place during wear. In one scenario, the architecture may be configured to amplify sound. For instance, one or more small microphones may be placed at selected points along the scaffolding (see, e.g., FIGS. 5A-B for examples). And one or more speakers may be formed by embedding an actuator in the body of the scaffolding itself so that the arrangement flexes with electrical stimulation. By way of example, the actuator could be a piezoelectric component or some other material As noted above, one or more different sensors may be arranged at different points along the scaffolding structure. This may include an EEG sensor, a MEG sensor, a heart rate sensor, a temperature sensor, an electrodermal activity (EDA) sensor, a pulse oximeter sensor, a glucometer, orientation sensors, location sensors, inertial measurement units (e.g., accelerometers), optical or infrared sensors, etc. can be used in any combination. Certain sensors can be disposed anywhere along the scaffolding structure, such as orientation, location and/or IMU sensors. In contrast, other sensors will be placed in contact with one or more portions of the ear all to benefit from direct contact with the underlying tissue. Such "contact" sensors may have preferred locations along the ear that have better electrical conductivity to the brain, better local blood flow, better acoustics, etc.

As seen in the examples of FIGS. 2-4, different scaffold structures have different sections or parts that are curved, angled, flat, etc. However, due to the nature of the ear, flat or nearly flat areas are relatively limited. Thus, according to one aspect a PC board or flexible circuitry can be arranged on different non-planar areas. However, for certain components such as integrated circuit elements or the battery, flatter surfaces are desirable. Such components may be placed at or near the saddle point between all the fingers in the examples of FIGS. 2-3, or along the bottom bowl of the concha region adjacent to the ear canal.

Example Systems

FIGS. 5A-C illustrate examples of how bio sensors tor EEG, EMG, ECG or other testing may be arranged on the scaffoldings of FIGS. 2-4. By way of example, different sensor contacts (e.g., electrodes or other sensors) 502, 504 and/or 506 may be arranged on or adjacent to the rear side of the scaffolding. As shown, the contacts, which may be any of the electrically conductive metal materials described above, can have different shapes, orientations and placements. The locations and configurations as shown are merely exemplary and may vary depending on the specific scaffolding structure, the type(s) of signals to be detected, placement of other components, etc.

While the above examples show the scaffolding arrangement for one ear, in some scenarios it is desirable to have sensor assemblies worn in both ears. Dual-ear arrangements may provide information that is local to one ear (e.g., a mono left/right auditory system), or that can best be seen with widely spaced electrodes (e.g., across/thru the head for EEG analysis). Dual-ear arrangements may also provide indications that received signals are in fact common to both ears and are thus not locally produced (e.g., ECG).

Figure 6A:
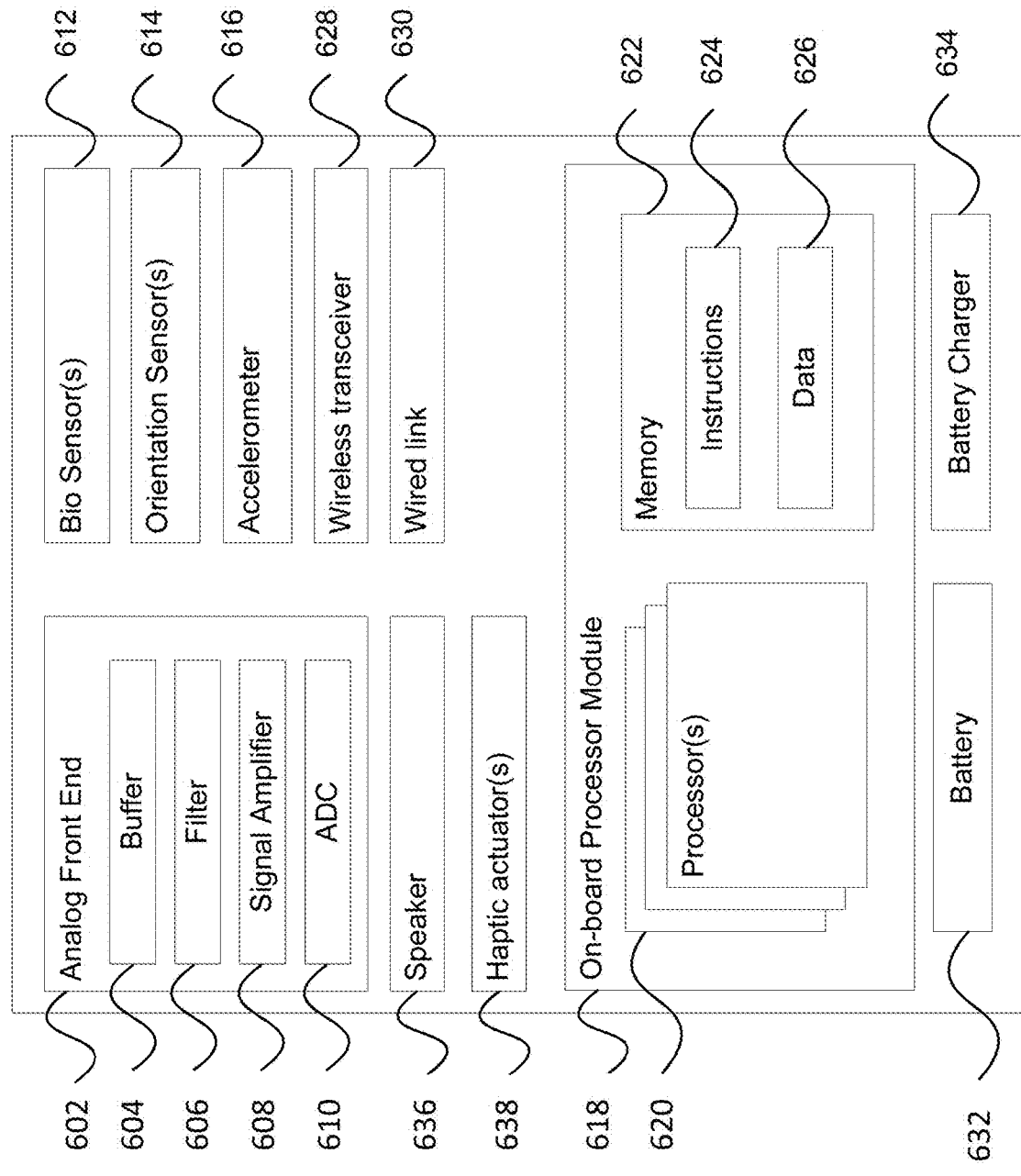
FIG. 6A illustrates an in-ear sensor assembly in accordance with aspects of the technology.
Figure 6B:
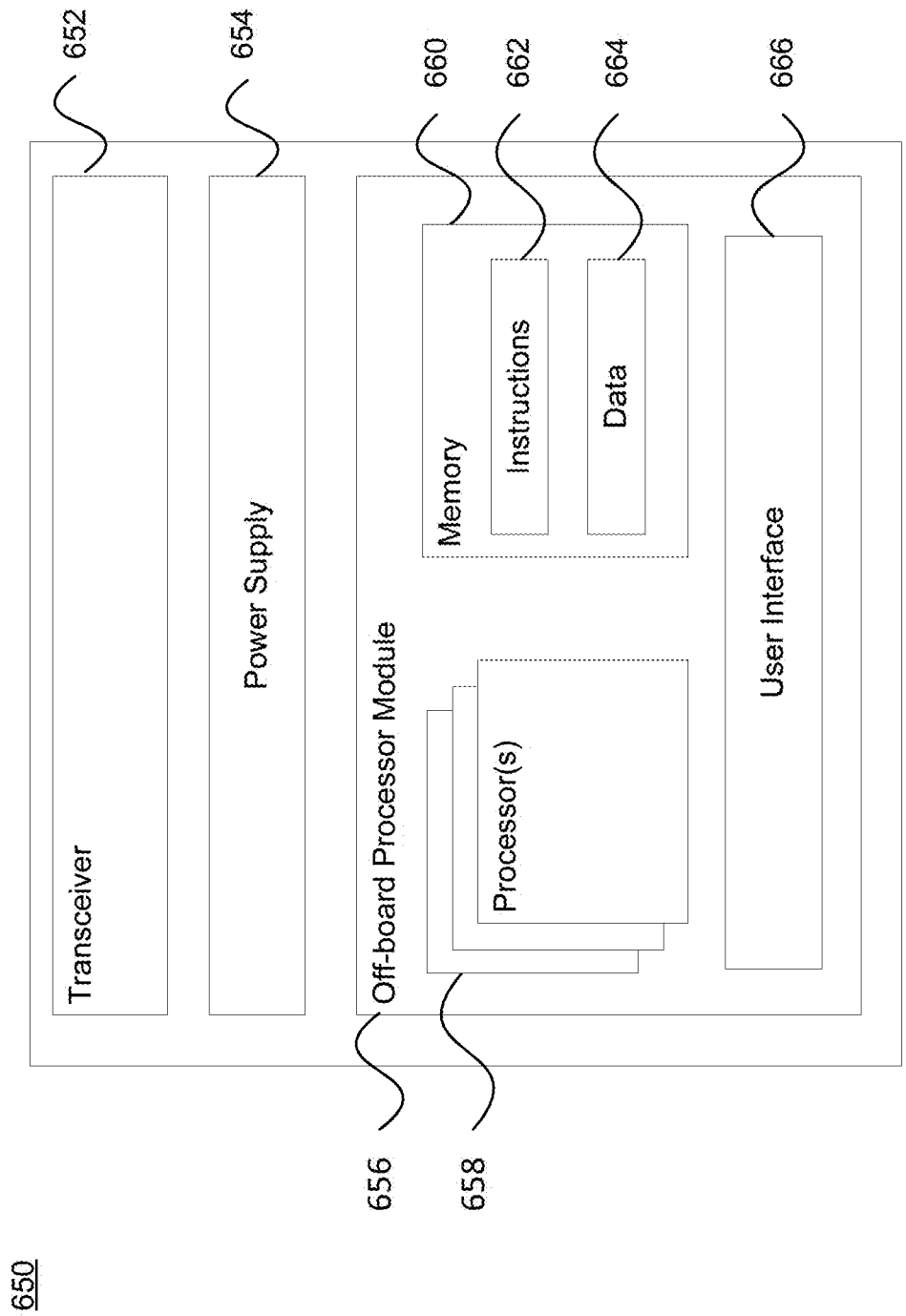
FIG. 6B illustrates an external processing system in accordance with aspects of the technology.

Upon insertion into the ear(s), the sensor assembly(ies) is configured to detect Alpha waves or other waves via the bio-sensors. Processing of such signals may be performed at the sensor assembly, by a remote processing system, or both. FIG. 6A illustrates one example of an on-board processing system 600, and FIG. 6B illustrates one example of a remote processing system 650. With regard to FIG. 6A, the signals from the sensor contacts may first be received by an analog front end (AFE) 602. The AFE 602 may provide one or more of signal buffering via buffer 604, filtering via filter(s) 606, signal amplification by amplifier 608, and/or analog to digital conversion by analog to digital converter (ADC) 610.

The processing system 600 may also receive biometric and other information from additional bio sensors 612, such as temperature, heart rate, EDA/galvanic skin response, pulse oximeter, glucometer and/or other sensors. Other sensors may include one or more orientation sensors 614 and an accelerometer 616. Some or all of the information from these other sensors may also be processed by AFE 602.

The processing system 600 may analyze the obtained data with an on-board processor module 618, which includes one or more processors 620 as well as memory 622 that stores instructions 624 and data 626 that may be executed or otherwise used by the processor(s) 620. The one or more processors 620 may be, e.g., a controller or CPU. Alternatively, the one or more processors 620 may be a dedicated device such as an ASIC, FPGA or other hardware-based device. The memory 622 may be of any type capable of storing information accessible by the processor(s) in a non-transitory manner, such as solid state flash memory or the like.

The instructions 624 may be any set of instructions to be executed directly (such as machine code) or indirectly (such as scripts) by the processor(s). For example, the instructions may be stored as computing device code in the non-transitory memory. In that regard, the terms "instructions" and "programs" may be used interchangeably herein. The instructions may be stored in object code format for direct processing by the processor(s), or in any other computing device language including scripts or collections of independent source code modules that are interpreted on demand or compiled in advance. The data 626 may be retrieved, stored or modified by one or more processors in accordance with the instructions 624. As an example, data 626 may include heuristics to be used when calibrating or evaluating electrode viability, for instance to rank electrode suitability based on signal-to-noise ratio or other metrics.

Alternatively or in addition to on-board signal analysis, the processing system may transmit the obtained data to remote processing system 650. This may be done, for instance, via a wireless transceiver 628 or a wired link 630, such as I2C, SPI, Universal Asynchronous Receiver/Transmitter (UART), I2S, or some other low-signal count communications path. In the former case, the wireless transceiver 628 may communicate with the remote processing system 650 via Bluetooth™, Bluetooth™ LE, near field communication (NFC) or some other wireless communication method. In the latter case, a flexible printed circuit or other wired link 630 may extend out the end of the sensor assembly and be physically coupled to remote processing system 650 that can receive and/or process the obtained bio signals.

System 600 also includes a battery 632 to power the components of the system. It may also include a battery charger 634. The battery charger may be contactless, or may be plugged into an external power source to charge the battery.

In one example a speaker 636 may be incorporated into the system 600. The speaker 636 is operatively coupled to the on-board processor module 618 to provide sound to the inner portions of the canal. The module 618 may actuate the speaker 636 to supplement (augment) sounds passed through the ear canal, or to generate different sounds such as audible cues (e.g., tones) to provide information or give aural feedback to the wearer. Alternatively or additionally, one or more haptic actuators 638 may be employed to give haptic feedback or other physical sensations to the wearer.

The system 600 may be incorporated into or mounted on the scaffold structure as a monolithic integrated circuit or as a set of discrete components. By way of example only, the AFE 602, sensors 612, 614 and 616, the battery 632, the battery charger 634, the speaker 636 and/or the haptic actuator(s) 638 need not be co-located with the on-board processor module 618. Rather, the individual components can be distributed across the scaffolding, for instance based on their size and shape, and whether they can be arranged on planar or non-planar portions of the scaffolding. Certain components may be added as different layers or regions of the scaffolding are being formed, for instance by 3D printing.

According to one scenario, a given scaffolding architecture combines the data collection from the various sensors with on-board processing and data link/storage elements. However, in other scenarios the scaffolding architecture may primarily gather sensor data and transmit it off-board for processing.

Turning to FIG. 6B, as shown remote processing system 650 includes a transceiver 652. The transceiver 652 is configured to communicate with one or both of wireless transceiver 628 and wired link 630. The system 650 also includes a power supply 654, which may include batteries and/or a connection for an outlet or the like. The information received from the on-board processing system 600, whether raw or unprocessed, is passed from the transceiver 652 to the off-board processor module 656.

The off-board processor module 656 is configured to analyze the obtained data with one or more processors 658 as well as memory 660 that stores instructions 662 and data 664 that may be executed or otherwise used by the processor(s) 658, in a manner similar to described above. The one or more processors 658 may be, e.g., a controller or CPU. Alternatively, the one or more processors 658 may be a dedicated device such as a DSP, an ASIC, FPGA or other hardware-based device. The memory 660 may be of any type capable of storing information accessible by the processor(s) in a non-transitory manner, such as solid state flash memory, hard disc, optical medium or the like. The off-board processor module 656 may also include a user interface subsystem 666, which may be used to present information regarding the processed data to the wearer, a technician, doctor or other authorized user.

As noted above, it may be desirable for the device(s) to be worn for extended periods of time. This can provide a wealth of information that can be used for different purposes, such as to obtain a general picture of person's health. One could evaluate temperature, including heat exchange between two points, as well as heat expulsion. The temperature may vary depending on whether the wearer is sleeping, sitting, moving, etc. Different kinds of brain activity can be measured and compared to what else is going on with the body.

In one test scenario, the sensor assembly could send sound through the ear, possibly in a manner that is not perceptible to the wearer, and measure the resultant brain activity. Information about heart rate variability or actions (e.g., chewing) can also be collected. Any or all of this information can provide context regarding the wearer's overall health. For instance, the information can be compared to a baseline for the particular wearer, which can be used as an assessment tool. In one particular example, one could evaluate the brain wave base line, plus voice analysis, plus heart rate and/or other signals for assessing mental health, the possibility of a stroke, a neurological condition, etc. The results of the assessment could be used for immediate treatment or to set up a treatment program (e.g., to help with anxiety or helping an autistic patient to focus on someone speaking to them.

In a further aspect of the technology, the scaffolding structure may be configured to match the skin color or skin tone of the user in response to some stimulus. In an example, one or more chromogenic materials may be applied as an outer layer or coating on the scaffolding. For instance, a chromogenic polymer may be applied as part of a 3D printing process. The chromogenic material may be photochromic, thermochromic or electrochromic, for example to adapt to be minimally visible. Thus, a photochromic material could automatically change color (e.g., tint or hue) as the amount of ambient light changes. A thermochromic material could change color in response to fluctuations in the wearer's skin temperature. And an electrochromic material may change color under electrical control, e.g., by the on-board processor module in response to some detected sensor input or estimated operating condition.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements. The processes or other operations may be performed in a different order or simultaneously, unless expressly indicated otherwise herein.

The invention claimed is:

1. A sensor assembly configured for partial or complete insertion in an ear of a wearer, the sensor assembly comprising:
    a central C-shaped body comprising one or more materials, the central C-shaped body having one or more protrusions configured to provide a spring force so that the sensor assembly maintains multiple points of contact along the ear of the wearer;
    one or more sensors disposed along the sensor assembly and attached to the central C-shaped body, the one or more sensors being configured to detect bio-signals via the ear of the wearer; and
    circuitry attached to the central C-shaped body and operatively coupled to the one or more sensors, the circuitry including a processing device configured to receive the detected bio-signals from the one or more sensors and to perform on-board processing of the received bio-signals or to transmit the received bio-signals to a remote processing system;
    wherein the central C-shaped body is configured to avoid sound occlusion by the sensor assembly when worn in the ear of the wearer.

2. The sensor assembly of claim 1, wherein the central C-shaped body is configured to self-center the sensor assembly in the ear of the wearer.

3. The sensor assembly of claim 1, wherein the one or more protrusions extend radially outward from the central C-shaped body.

4. The sensor assembly of claim 3, wherein the one or more sensors are disposed along the protrusions.

5. The sensor assembly of claim 1, further comprising an extension extending from the central C-shaped body, the extension configured to extend at least partly into the ear canal during wear.

6. The sensor assembly of claim 5, wherein at least one of the one or more protrusions extends from the central C-shaped body at an angle relative to the extension.

7. The sensor assembly of claim 6, wherein the one or more sensors are disposed along at least one of the extension and the one or more protrusions.

8. The sensor assembly of claim 6, wherein a first one of the one or more protrusions forms a first end of the C-shaped body, and the extension forms an opposing, second end of the C-shaped body.

9. The sensor assembly of claim 1, wherein the central C-shaped body includes a series of openings along the body disposed therealong.

10. The sensor assembly of claim 1, wherein the one or more materials includes a first material having a first hardness and a second material having a second hardness less than the first hardness.

11. The sensor assembly of claim 10, wherein the first material forms a base layer of the C-shaped body, and the second material being over-molded on the first material.

12. The sensor assembly of claim 1, wherein the C-shaped body is formed by 3D printing or injection molding.

13. The sensor assembly of claim 1, wherein the one or more materials includes one or more bio-compatible materials arranged along points of contact with the ear of the wearer.

14. The sensor assembly of claim 1, wherein the circuitry includes a plurality of components distributed along different areas of the central C-shaped body.

15. The sensor assembly of claim 1, wherein the individual ones of the one or more protrusions are configured to provide the spring force at different anchor points about one or more of the ear's helix, antihelix, concha or opening to the ear canal.

16. The sensor assembly of claim 1, wherein an extension of the C-shaped body has a channel configured to extend at least partly into the ear canal.

17. The sensor assembly of claim 16, wherein the channel is configured to extend along the first bend of the ear canal.

18. The sensor assembly of claim 17, wherein the channel is configured to extend past the first bend and at least partly along the second bend of the ear canal.

19. The sensor assembly of claim 1, wherein the C-shaped body is at least partly covered by a chromogenic material configured to change color in response to a stimulus.

20. A sensor system configured to detect and process bio signals of a wearer, the sensor system comprising:
the sensor assembly of claim 1; and
a remote processing system including a transceiver configured for communication with a transceiver of the sensor assembly, and one or more processors configured to process the bio signals received from the sensor assembly.

* * * * *